(12) United States Patent
Daw et al.

(10) Patent No.: US 12,076,498 B2
(45) Date of Patent: Sep. 3, 2024

(54) CARRYING AND STORAGE CASE FOR EXTERNAL CATHETER SYSTEM

(71) Applicant: C. R. Bard, Inc., Franklin Lakes, NJ (US)

(72) Inventors: Kyle Daw, Smyrna, GA (US); Shahab Siddiqui, Lawrenceville, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 17/524,378

(22) Filed: Nov. 11, 2021

(65) Prior Publication Data

US 2022/0152343 A1    May 19, 2022

Related U.S. Application Data

(60) Provisional application No. 63/115,505, filed on Nov. 18, 2020.

(51) Int. Cl.
*A61M 25/00* (2006.01)

(52) U.S. Cl.
CPC ....... *A61M 25/002* (2013.01); *A61M 2209/06* (2013.01); *A61M 2209/08* (2013.01)

(58) Field of Classification Search
CPC .......... A61M 2209/06; A61M 2209/08; A61M 25/002; A61M 2209/082; A61M 2209/084; A45C 13/02; A61B 50/312
USPC ................................. 206/223–570, 472–475
See application file for complete search history.

(56) References Cited

U.S. PATENT DOCUMENTS

| | | | | |
|---|---|---|---|---|
| 1,009,047 | A * | 11/1911 | Capitain | A61B 50/30 206/572 |
| 2,425,963 | A * | 8/1947 | Silva | A45C 11/20 206/408 |
| 4,631,061 | A * | 12/1986 | Martin | A61F 5/451 604/323 |
| 5,845,780 | A * | 12/1998 | Allen | A45C 3/00 190/110 |
| 6,740,066 | B2 * | 5/2004 | Wolff | A61F 5/451 604/323 |
| 7,987,626 | B2 * | 8/2011 | Williams | F41A 29/02 42/95 |
| 8,006,846 | B2 * | 8/2011 | Robertson | A45C 13/02 206/479 |
| 8,046,848 | B2 * | 11/2011 | Birbara | A61G 9/006 4/144.1 |
| 9,259,593 | B2 * | 2/2016 | Roach | A61N 1/3968 |
| 10,820,673 | B1 * | 11/2020 | Blauer | A45C 5/03 |
| 11,612,448 | B2 * | 3/2023 | Gustafson | A45C 13/02 206/570 |
| 2007/0084742 | A1* | 4/2007 | Miller | A61B 50/20 206/438 |

(Continued)

*Primary Examiner* — Chun Hoi Cheung
(74) *Attorney, Agent, or Firm* — Rutan & Tucker LLP

(57) ABSTRACT

A case for a catheter system is disclosed, the case including a case body including a first side coupled to a second side. The case can include padding with a plurality of cavities to receive components of the catheter system and a strap to secure components of the catheter system to an interior of the case body. The case can further include one or more clips affixed to an interior wall of the first side or the second side of the case body. The one or more clips can be configured to secure additional catheter tubing or an external catheter to the interior wall of case body.

7 Claims, 6 Drawing Sheets

(56) References Cited

U.S. PATENT DOCUMENTS

| | | | |
|---|---|---|---|
| 2010/0059560 A1* | 3/2010 | Lanum | A61B 50/31 224/257 |
| 2013/0277262 A1* | 10/2013 | Nemard | A61B 50/31 206/438 |
| 2017/0197047 A1* | 7/2017 | Minato | A61M 16/0078 |
| 2022/0002061 A1* | 1/2022 | Cotte | B65D 5/241 |

* cited by examiner

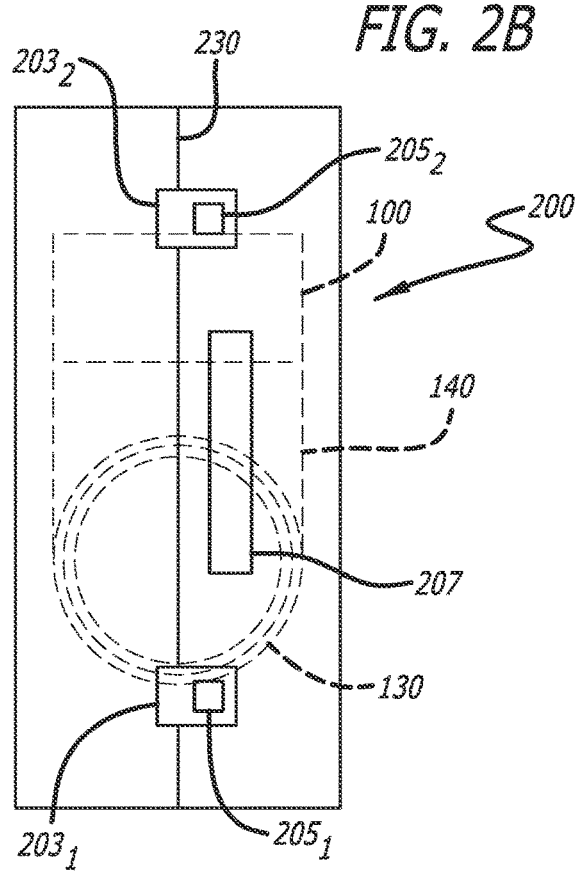
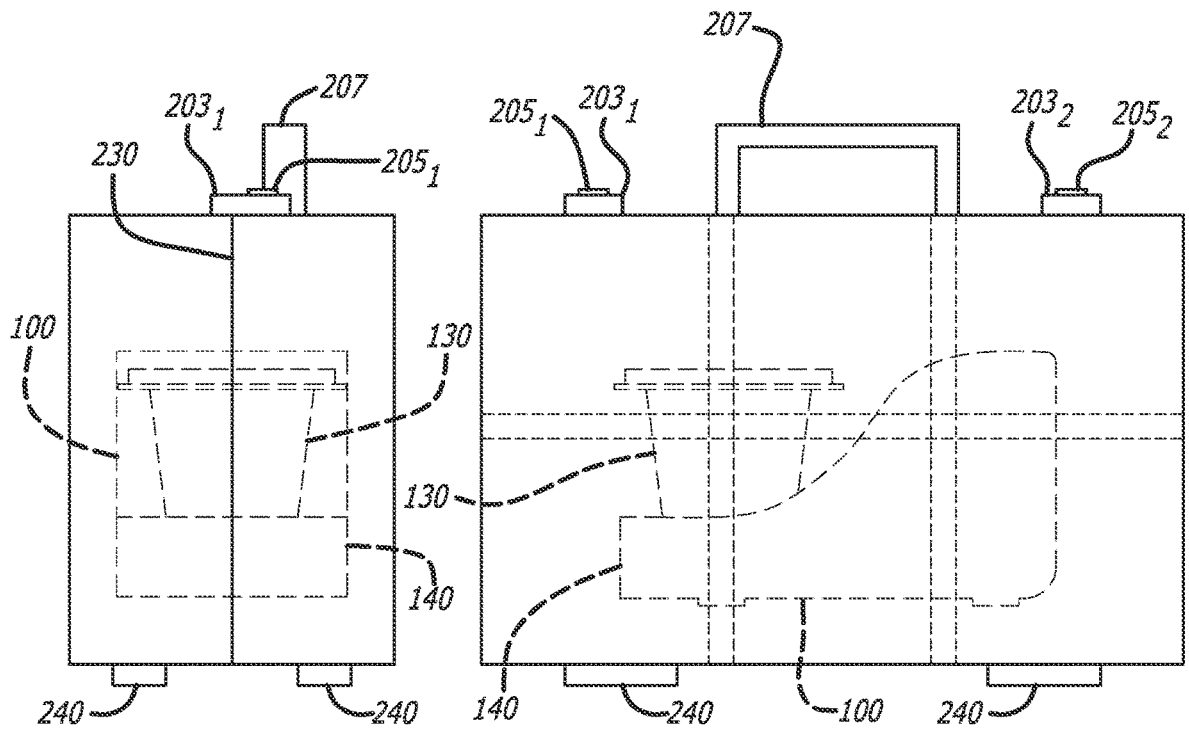

CARRYING AND STORAGE CASE FOR EXTERNAL CATHETER SYSTEM

PRIORITY

This application claims the benefit of priority to U.S. Provisional Application No. 63/115,505, filed Nov. 18, 2020, which is incorporated by reference in its entirety into this application.

SUMMARY

Briefly summarized, embodiments disclosed herein are directed to systems, methods, and apparatuses for carrying and storing external catheters, pumps, and associated accessories, and providing privacy for patients.

One problem that may arise with external catheters and pumps is providing a convenient, secure, and efficient way to transport the catheter and pump system. In particular, an external catheter and pump system may be inefficient to transport, for example a canister associated with the pump could fall from its pump base. Since the canister contains bodily fluids, such a fall potentially creates an unsanitary mess. Moreover, in order to avoid such a mishap, a patient must transport the catheter and pump system slowly and with great care.

A second problem is storing the external catheter and/or pump system when not in use. A third problem is providing privacy and discretion while the external catheter and pump system is in use. In particular, if the external catheter is a urinary catheter, patients may not want to be observed using the catheter. In some cases, patients may not even want others to be aware they use a urinary catheter. These problems may be especially pronounced if patients use the catheter in their homes, where they wish to go about normal life, entertain visitors, and the like.

Disclosed herein is a case for a catheter system. The catheter system can comprise a catheter and a pump. The case has, in some embodiments, a main compartment, a closeable main seam, and a carrying grip. The main compartment is operative to contain the catheter system. The closeable main seam is operative to provide access to the main compartment.

In some embodiments, the main compartment of the case comprises storage pockets or clips operative to store catheters or catheter tubing.

In some embodiments, the carrying grip comprises a carrying handle or a carrying strap.

In some embodiments, the catheter system further comprises a canister. The main compartment of the case is further operative to contain the canister.

In some embodiments, the main compartment comprises a support operative to maintain the catheter system in a stable position within the main compartment.

In some embodiments, the support comprises one or more of an adjustable strap or a fixed guiding strip. The adjustable strap can be operative to constrain motion of the catheter system. The fixed guiding strip can be operative to maintain a position or orientation of the catheter system.

In some embodiments, the support comprises a form fitting the main compartment. The catheter system is maintained in the stable position within a cavity of the form.

In some embodiments, the form further comprises a second cavity for a pump battery. In some embodiments, the form further comprises a third cavity for a pump electrical cord.

In some embodiments, the main compartment is further operative to conceal the catheter system.

In some embodiments, the main compartment is further operative to contain the catheter system while the pump is in operation.

In some embodiments, the main compartment is further operative to conceal an odor of the catheter system.

In some embodiments, the closeable main seam comprises a passage for a catheter tube. In some embodiments, the closeable main seam comprises a passage for an electrical cord.

In some embodiments, the main compartment comprises a cavity for a catheter tube and/or an electrical cord. The cavity can provide a passage out of the case for the catheter tube and/or the electrical cord.

In some embodiments, the case further comprises padding operative to protect the catheter system from mechanical shocks.

Also disclosed herein is a method of containing a catheter system comprising a catheter and a pump. The method includes, in some embodiments, containing the catheter system in a case. The case has, in some embodiments, a main compartment, a closeable main seam, and a carrying grip. The main compartment is operative to contain the catheter system. The closeable main seam is operative to provide access to the main compartment.

In some embodiments, the method further comprises transporting the case or storing the case.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which:

FIG. 2B shows a top projection view of a carrying and storage case for a catheter and pump system according to some embodiments;

FIG. 2C shows a side projection view of a carrying and storage case for a catheter and pump system according to some embodiments;

FIG. 2D shows a front projection view of a carrying and storage case for a catheter and pump system according to some embodiments;

DETAILED DESCRIPTION

Figure 1:
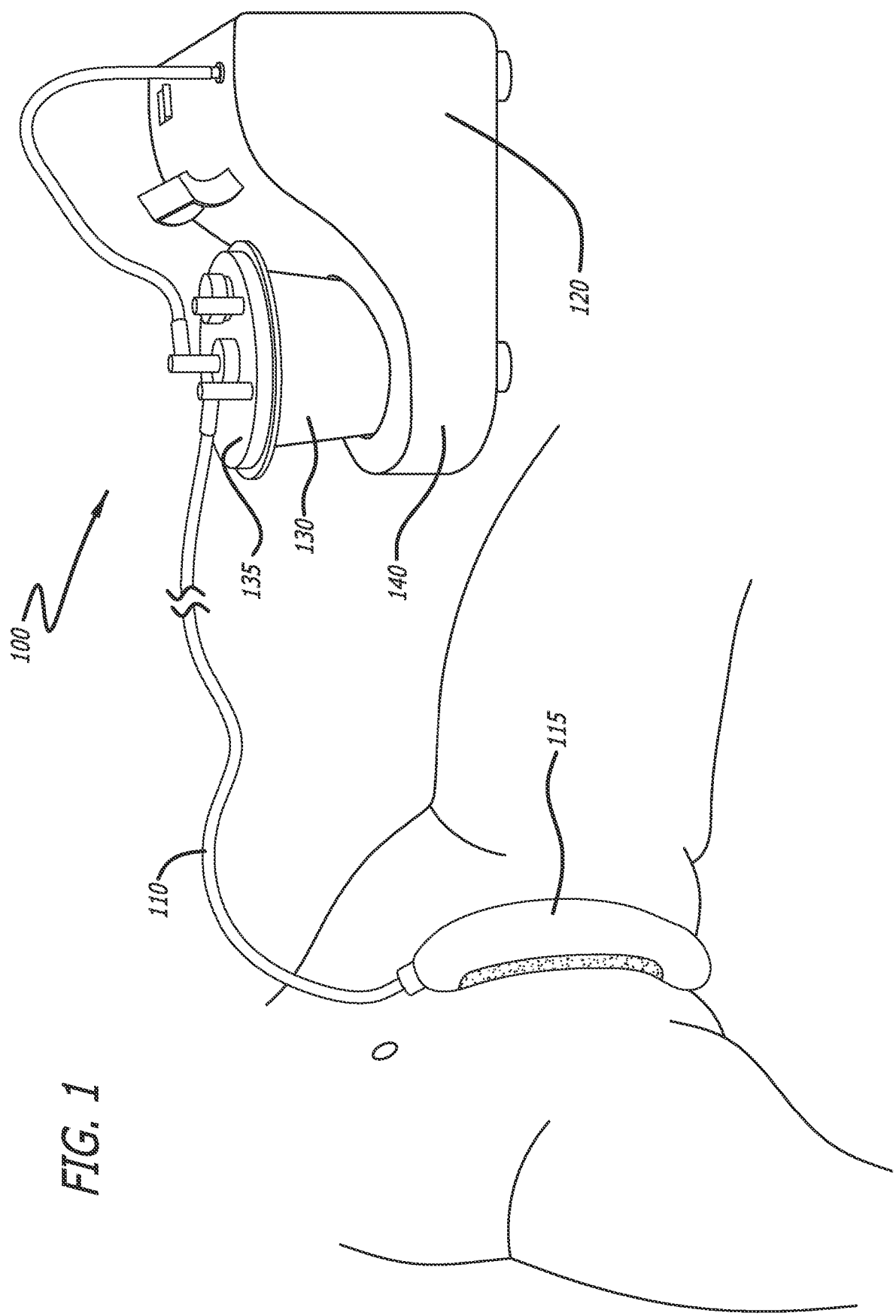
FIG. 1 displays an external catheter and pump system according to some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Referring to FIG. 1, an external catheter and pump system 100 is displayed, according to some embodiments. In this example, catheter tube 110 terminates in urinary catheter 115, such as a female external catheter (e.g., PureWick™ Female External Catheter, BD), which can be inserted over the urethra of a patient with bladder incontinence. Electric pump 120 can pump the patient's urine through tubing 110, thereby gently "wicking" urine away from the patient. Pump 120 can pump the wicked urine to collection canister 130, which can be covered by lid 135. For patients with bladder incontinence, catheter and pump system 100 can be a safe, convenient, and effective way to catheterize.

However, external catheter and pump system 100 may pose challenges to being transported, for example canister 130 could fall from pump base 140. Since canister 130 can contain bodily fluids, such a fall potentially creates an unsanitary mess. Moreover, in order to avoid such a mishap, a patient must transport the catheter and pump system slowly and with care. Accordingly, an effective solution is needed to transport catheter and pump system 100.

In addition, some patients may prefer not to be observed using catheter and pump system 100. In some cases, patients may prefer for others to be unaware they use a urinary catheter. These desires may be particularly strong if patients use system 100 at home, where they wish to go about normal life, entertain visitors, and the like. Likewise, in a hospital, patients may have shared accommodations, and may be especially concerned about protecting their privacy from strangers. Aside from privacy concerns, some patients may simply consider the system, especially canister 130, to be unpleasant or unhygienic while in use. Accordingly, a solution is needed to provide privacy and discretion while external catheter and pump system 100 is in use. Finally, a convenient method is needed for storing catheter and pump system 100 when not in use. Disclosed herein is a system that addresses these needs.

Figure 2A:
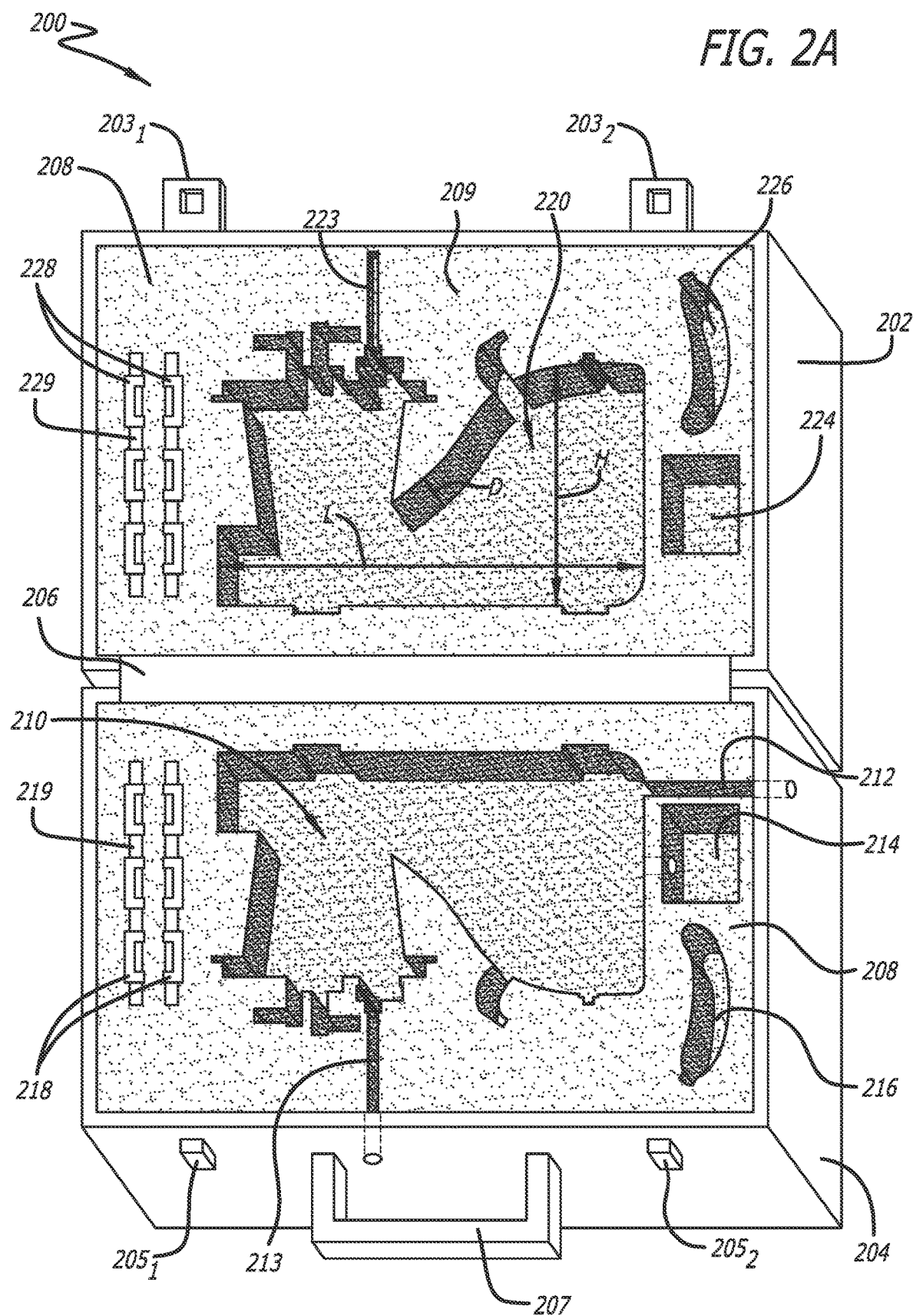
FIG. 2A illustrates an exemplary carrying case for the external catheter and pump system of FIG. 1 according to some embodiments.

Referring now to FIG. 2A, an exemplary carrying case 200 for the external catheter and pump system of FIG. 1 is shown, according to some embodiments. In various examples, case 200 can be used for transporting or storing the external catheter and pump system, or for covering the catheter and pump system while in use.

Case 200 can open along a main seam separating top side 202 and bottom side 204, also referred to as top and bottom flaps. Top side 202 and bottom side 204 can be connected by binding 206, which allows case 200 to swing open and closed. In some embodiments, the binding 206 may include one or more hinges such that the binding 206 hingedly couples the top side 202 to the bottom side 204. When case 200 is closed, top side 202 can be adjoined to bottom side 204 by fastening the top clasp components $203_1$-$203_2$ to the bottom clasp components $205_1$-$205_2$. It should be understood that other closure mechanisms may be utilized, such as a zippered closure.

Carrying handle 207 may be securely attached to case 200. In this example, handle 207 is situated on bottom side 204, but in various embodiments handle 207 can be placed on either top side 202 or bottom side 204 of case 200. In some embodiments, carrying handle 207 may be long or retractable, e.g., so that case 200 can be rolled. In some embodiments, case 200 can have a carrying strap instead of, or in addition to, handle 207 (see FIG. 3B).

In some embodiments, the bottom side 204 can contain a filling, such as foam or padding 208, and top side 202 can contain a filling, such as foam/padding 209, to protect the catheter and pump system from mechanical shocks. In an embodiment, foam/padding 208 and 209 may be shaped in a form to fit the catheter and pump system in a specific position, thereby stabilizing and securing the system, and further protecting it from shocks or shifting unintentionally, which could result in spills of urine contained within the collection canister 130. In particular, in this example, foam/padding 208 and 209 are shaped to include a bottom pump system cavity 210 and top pump system cavity 220. Accordingly, the foam/padding and/or the cavities may also be referred to as forms. In one embodiment, the pump system cavity 210 can have dimensions as shown in FIG. 2A, where length (L) is 13 inches, height (H) is 9.5 inches and depth (D) is 4.75 inches.

In an embodiment, foam/padding 208 and 209 may contain additional cavities. For example, bottom power cord cavity 212 can provide space for a power cord of the catheter and pump system. Bottom tubing cavity 213 and top tubing cavity 223 are cavities for tubing that may extend out of case 200, for example while the pump system is in use (see FIG. 3D). In an embodiment, tubing cavities 213 and 223 may be located in another part of case 200, or the foam/padding 208 and 209 may contain multiple tubing cavities. For example, a tubing cavity may be located closer to binding 206, such that tubing from the pump canister can lead more directly to the catheter while it is in use.

Optionally, foam/padding 208 may also contain bottom battery cavity 214, and/or foam/padding 209 may contain top battery cavity 224, to store a battery for the catheter and pump system. Likewise, bottom catheter cavity 216 and top catheter cavity 226 may be used to store additional replacement catheters, and bottom clips 218 and top clips 228 can hold additional replacement tubing 219 and 229.

Referring to FIG. 2B, a top projection view of a carrying and storage case 200 for a catheter and pump system 100 is shown, according to some embodiments. Case 200 may open along a middle seam 230 that can house accessories or additional catheters and tubing. In an example, the exterior of case 200 can comprise a flexible material, such as nylon, so that the two sides of middle seam 230 can meet when case 200 is closed. Alternatively, the exterior can comprise an inflexible material, such as leather or plastic.

In some embodiments, part or all of the interior of case 200 may be padded, so as to protect catheter and pump system 100 from mechanical shocks (see FIG. 2A). In some embodiments, the interior of case 200 may be insulated, so as to mask odors or sound from the catheter and pump system 100, especially while in use, and/or to protect against spills while being transported. For example, the interior of case 200 may be waterproof, soundproof, thermally insulated, etc. In an embodiment, the exterior of case 200 may also be waterproof, insulated, or padded.

Case 200 may include a carrying handle 207 as in the example of FIG. 2A above, and/or may include other carrying accessories such as a carrying strap. Supports 240 (on the underside of case 200) can rest case 200 on a floor, the ground, or another surface. In an embodiment, supports 240 can include wheels and/or casters so that case 200 can be rolled along a surface. In an embodiment, carrying handle 207 may be long or retractable, so that case 200 can be rolled while in an upright position and/or while oriented vertically. In an embodiment, supports 240 and/or the wheels may also be adjustable and/or retractable.

In an embodiment, the main seam is not necessarily located in the center of the cross-section of case 200. For example, case 200 may open from a front face, such that the main seam 230 may be located on the left or right sides of FIG. 2B.

FIG. 2C shows a side projection view of a carrying and storage case 200 for a catheter and pump system, according to some embodiments. As shown, the catheter and pump system can be housed in case 200 in an upright position. Alternatively, the catheter and pump system may be housed on its side, or in any other orientation or position.

Case 200 can securely fasten the pump system so that it can be transported with minimal risk. In this example, canister 130 can remain in its position in the pump base, as also shown in the example of FIG. 1 above. In some embodiments, the case 200 may include supports or other features to stabilize or secure canister 130 and to prevent it from falling. For example, case 200 may include straps, loops, pockets, strips, struts, and/or walls to stabilize canister 130. In some embodiments, such features may stabilize canister 130 while positioned within the pump base 140, whereas in other embodiments, the features may stabilize canister 130 separately. For example, in the case of a pocket or loop support, canister 130 may be removed from pump base 140 and be stored separately in the pocket or loop. In some embodiments, such stabilizing features may be adjustable. For example, the supports' size and shape may be adjusted, and/or the supports may be opened or closed, using buttons, snaps, hooks, Velcro, and the like (e.g., straps 255-257 in FIG. 2D). In some embodiments, case 200 may include similar features to stabilize or secure the pump base 140, or any other part of the catheter and pump system. In some embodiments, these supports or other stabilizing features can also protect the various components of the catheter and pump system from mechanical shocks.

FIG. 2D shows a front projection view of a carrying and storage case 200 for a catheter and pump system, according to some embodiments. In this example, the catheter and pump system is housed upright within case 200. Canister 130 can remain in the pump base 140, as shown in the example of FIG. 1. In some embodiments, the case 200 may include features to stabilize or secure canister 130 to maintain its position, for example on the pump base 140, such as straps 255-257. For example, case 200 may be largely hollow, like a suitcase, but have straps 255-257 and/or loops to constrain any motion of the components of the catheter and pump system. In another example, case 200 may contain a form to fit the catheter and pump system in a specific position, such as pump system cavities 210 and 220 in FIG. 2A, thereby stabilizing and securing the system, and protecting it from shocks. Case 200 may also contain padding to protect the components of the catheter and pump system (see FIG. 2A). In an embodiment, the fitted form may be insulated and/or padded, as described in the example of FIG. 4 above.

Figure 3A:
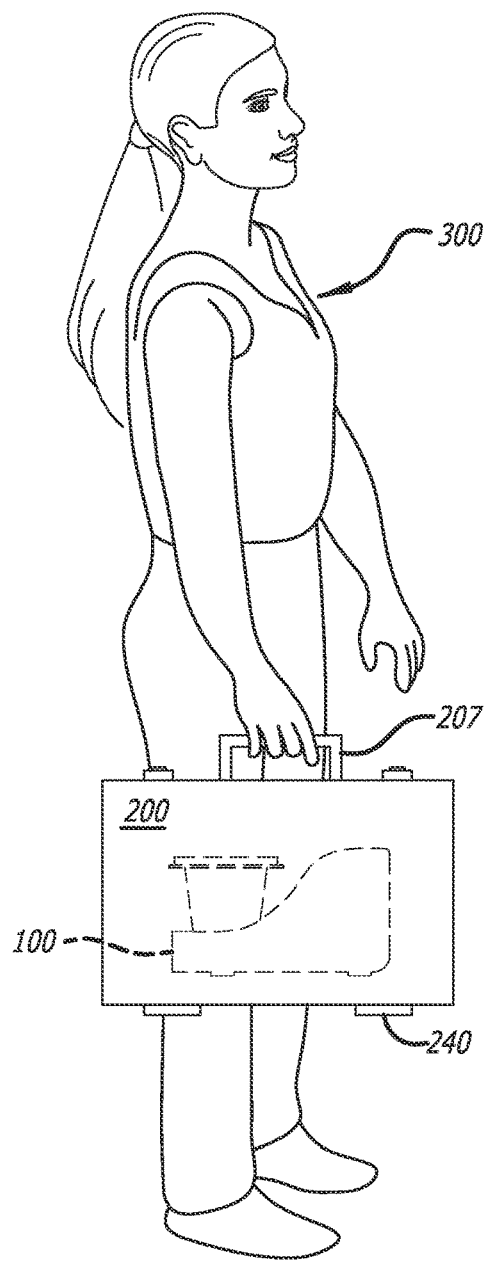
FIG. 3A illustrates transporting the catheter and pump system with the carrying case of FIGS. 2A-2D, according to some embodiments.

Referring to FIG. 3A, transporting the catheter and pump system 100 with a carrying case 200 is illustrated, according to some embodiments. User 300 carries case 200 via handle 207, which is securely attached to the case. In this example, the catheter and pump system 100 is housed upright within case 200. By using case 200, user 300 can prevent the canister of system 100 from falling off of the pump base while being transported, thereby enabling system 100 to be transported in a sanitary as well as convenient manner.

Likewise, case 200 facilitates transporting system 100. For example, all of the component parts and accessories of catheter and pump system 100 are enclosed together in case 200, making it easy for user 300 to pick up the entire system without misplacing any items. Moreover, user 300 can rest case 200 on the ground or floor using supports 240, or in some embodiments can roll case 200 on wheels. In another example, user 300 can put system 100 away while in transit, e.g. on the floor of a car or a luggage compartment of an airplane, train, or bus, without concern of mishap or loss of privacy.

In another example, catheter and pump system 100 can be housed within case 200 in any other orientation, such as on its side. Alternatively, the components of the catheter and pump system 100 may be stored separately, for example in separate compartments or pockets, or be stored in any other way, and are not limited by the present disclosure.

In an embodiment, case 200 may open along a middle seam. Such a middle seam can also store accessories or additional catheters and tubing, for example along the interior of the side flaps of case 200. Accordingly, user 300 can conveniently transport all the components and accessories of catheter and pump system 100 together in case 200.

Figure 3B:
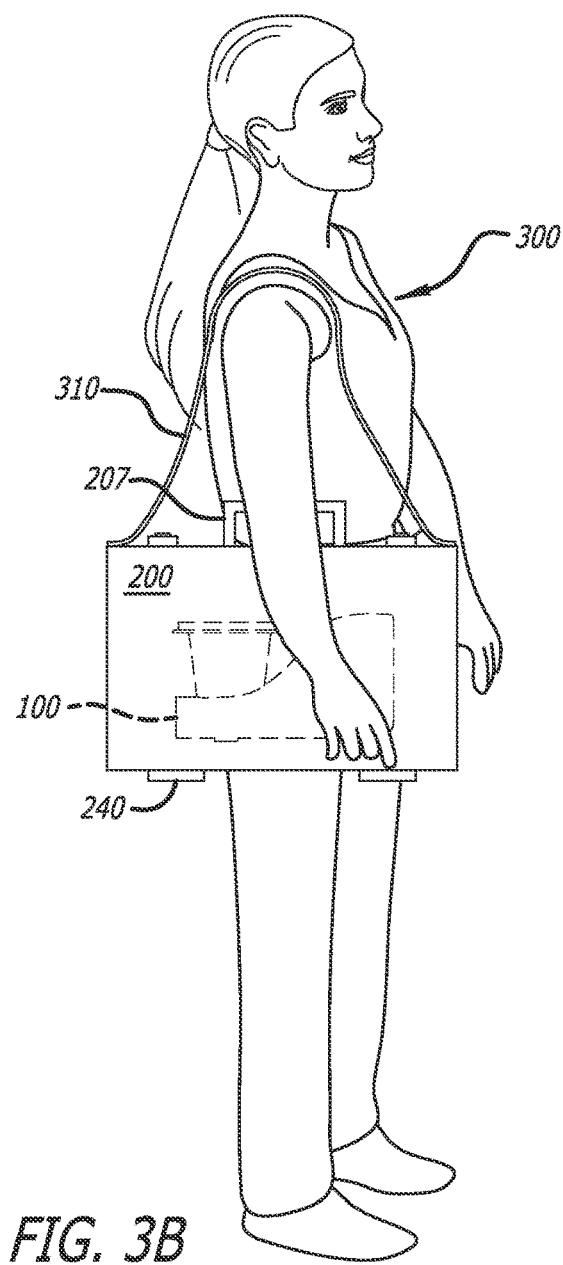
FIG. 3B illustrates the carrying case of FIGS. 2A-2D with a strap, according to some embodiments.

FIG. 3B illustrates a carrying case 100 with a carrying strap 310, according to some embodiments. In this example, a user 300 can carry case 100 via carrying strap 310 over the user's shoulder. User 300 may use strap 310 to carry case 100 while walking, standing, waiting in line, as a carry-on in an airplane, bus, or other conveyance, etc. In various embodiments, case 100 may have both carrying strap 310 and a carrying handle, as in the example of FIG. 3A, or may have only carrying strap 310 or a carrying handle. In some embodiments, the carrying handle and/or strap 310 may be removable or otherwise adjustable, for example, the position, size, or tension of carrying strap 310 may be adjustable.

Figure 3C:
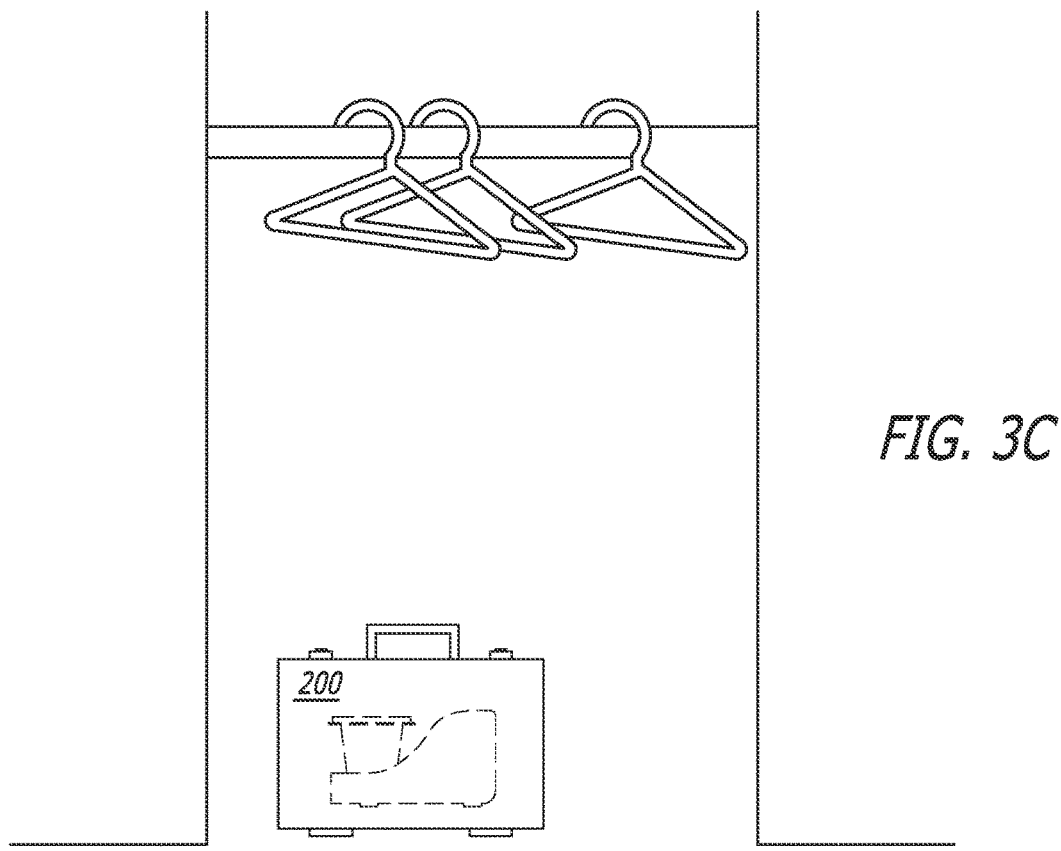
FIG. 3C illustrates storing the catheter and pump system in the carrying case of FIGS. 2A-2D, according to some embodiments.

FIG. 3C illustrates storing the catheter and pump system 100 with a storage case 200, according to some embodiments. In addition to being used to transport the catheter and pump system 100, as in the examples of FIGS. 3A and 3B above, case 200 can also function to store catheter and pump system 100 when not in use.

In particular, storage case 200 can provide a sense of privacy for a user by concealing system 100, for instance while stored in a patient's home. In this example, catheter and pump system 100 is stored in a closet 320. For various reasons, a patient might store catheter and pump system 100, e.g. in a clothes closet, coat closet, or medicine cabinet in her home. For example, the patient's home might not have an attic or storage space, closet 320 might be conveniently accessible from the patient's bedroom when the patient needs to use catheter and pump system 100, or the patient might store system 100 in closet 320 in order to move system 100 out of the way and to save space in the patient's bedroom. However, since family members or guests are likely to access closet 320, the patient may wish to conceal catheter and pump system 100 so that these others will not inadvertently notice it. Likewise, if catheter and pump system 100 is stored elsewhere, such as in the patient's bedroom or another living space, in the patient's vehicle trunk or wheelchair, or must be carried for the patient by a taxi driver or hotel employee, the patient may be concerned for her privacy or discretion. Accordingly, storage case 200 can address this need by keeping the components of catheter and pump system 100 out of sight. In an example, case 200 can even be locked e.g., with a padlock, or even include a built-in lock, to protect the patient's privacy and protect against loss or theft.

In addition, storage case 200 can function to organize the catheter and pump system 100. Because catheter and pump system 100 is kept in storage case 200, all the component parts and accessories of system 100 are enclosed together in one place, and thus unlikely to be misplaced. By the same token, such components are also unlikely to intermix or be confused with other items being stored in closet 320, such as items on the closet floor or shelves. If catheter and pump system 100 is used in a hospital, case 200 can keep important items like additional catheter tubes in close proximity to catheter and pump system 100, while also organizing these items so a hospital employee can efficiently pick them up and return them to a storage closet. When additional catheters and tubes are needed, the patient or medical personnel can easily find and access them in case 200.

Figure 3D:
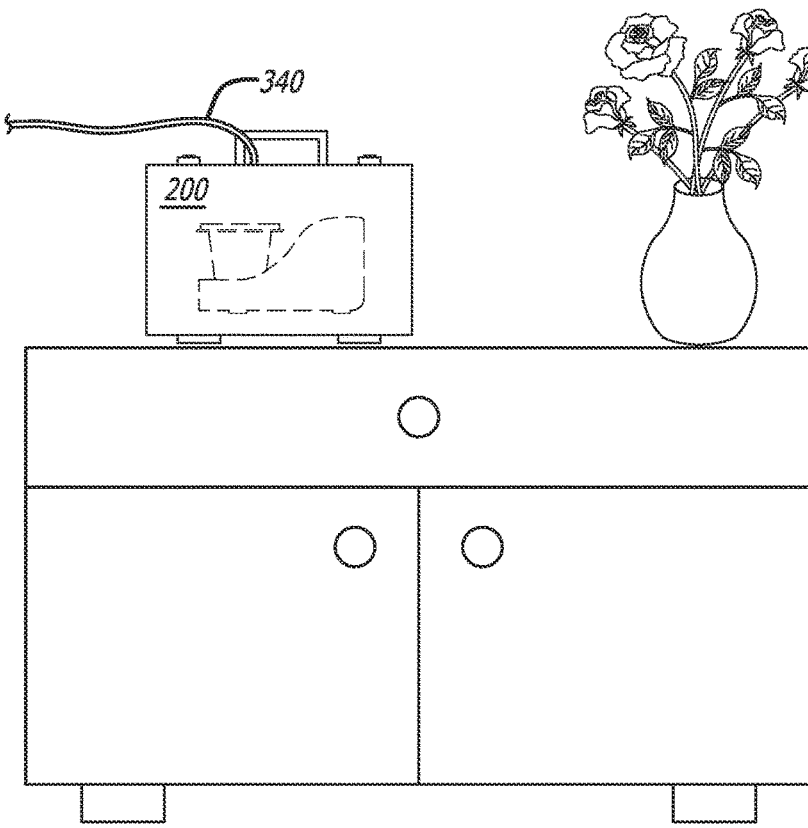
FIG. 3D illustrates the catheter and pump system included within the carrying case of FIGS. 2A-2D for discretion, according to some embodiments.

FIG. 3D illustrates covering the catheter and pump system 100 for discretion while in use in an environment 330 (e.g., a public environment or gathering of people) with covering case 200, according to some embodiments. In addition to its uses for transporting and storing the catheter and pump system 100, as in the examples above, covering case 200 can also function to conceal system 100 while system 100 is in active use, thereby providing a sense of privacy for a patient.

Some patients may prefer not to be observed using catheter and pump system 100. In some cases, patients may prefer for others to be unaware they use a urinary catheter. These desires may be particularly strong if patients use system 100 at home, where they wish to go about normal life, entertain visitors, and the like. Likewise, in a hospital, patients may have shared accommodations, and may be especially concerned about protecting their privacy from strangers.

For example, a patient may not wish for the canister containing her urine to be visible while catheter and pump system 100 is in use. In addition to privacy concerns, the patient may simply consider the canister to be unpleasant or unhygienic. By covering catheter and pump system 100, covering case 200 can conceal the canister and all other components of system 100. Likewise, when catheter and pump system 100 is in active use, covering case 200 can assist in masking urinary odors from the canister of catheter and pump system 100. Moreover, pump system 100 may produce noise, such as motor noise, while it pumps. Covering case 200 can also muffle such noise. Accordingly, covering case 200 can address privacy concerns by obscuring or masking the appearance, sounds, and odors from catheter and pump system 100. In some embodiments, covering case 200 may be insulated, so as to conceal odors or noise from the catheter and pump system 100.

In this example, catheter tubing 340 can lead from system 100, which is situated inside case 200, to the urinary catheter, which can be placed in a patient, for example a patient reclining in her own bed at home. In an embodiment, case 200 can have an opening designed for tubing 340. In another embodiment, case 200 can have other designed features to allow tubing 340 to pass out of case 200. For example, a main seam of covering case 200 can be closed by a zipper, which can be partially opened for tubing 340 while catheter and pump system 100 is in use. Alternatively, the main seam can be closed by buttons, snaps, hooks, Velcro, and the like, in a manner that leaves passages for tubing 340. In an embodiment, case 200 can include a combination of such features, for example both a zipper and a dedicated passage for tubing 340, and is not limited by the present disclosure. Likewise, case 200 can have an opening or other designed features to allow a power cord to pass from the pump out of case 200, thereby connecting the catheter pump inside case 200 to a wall electrical outlet while the pump is in operation.

Figure 4:
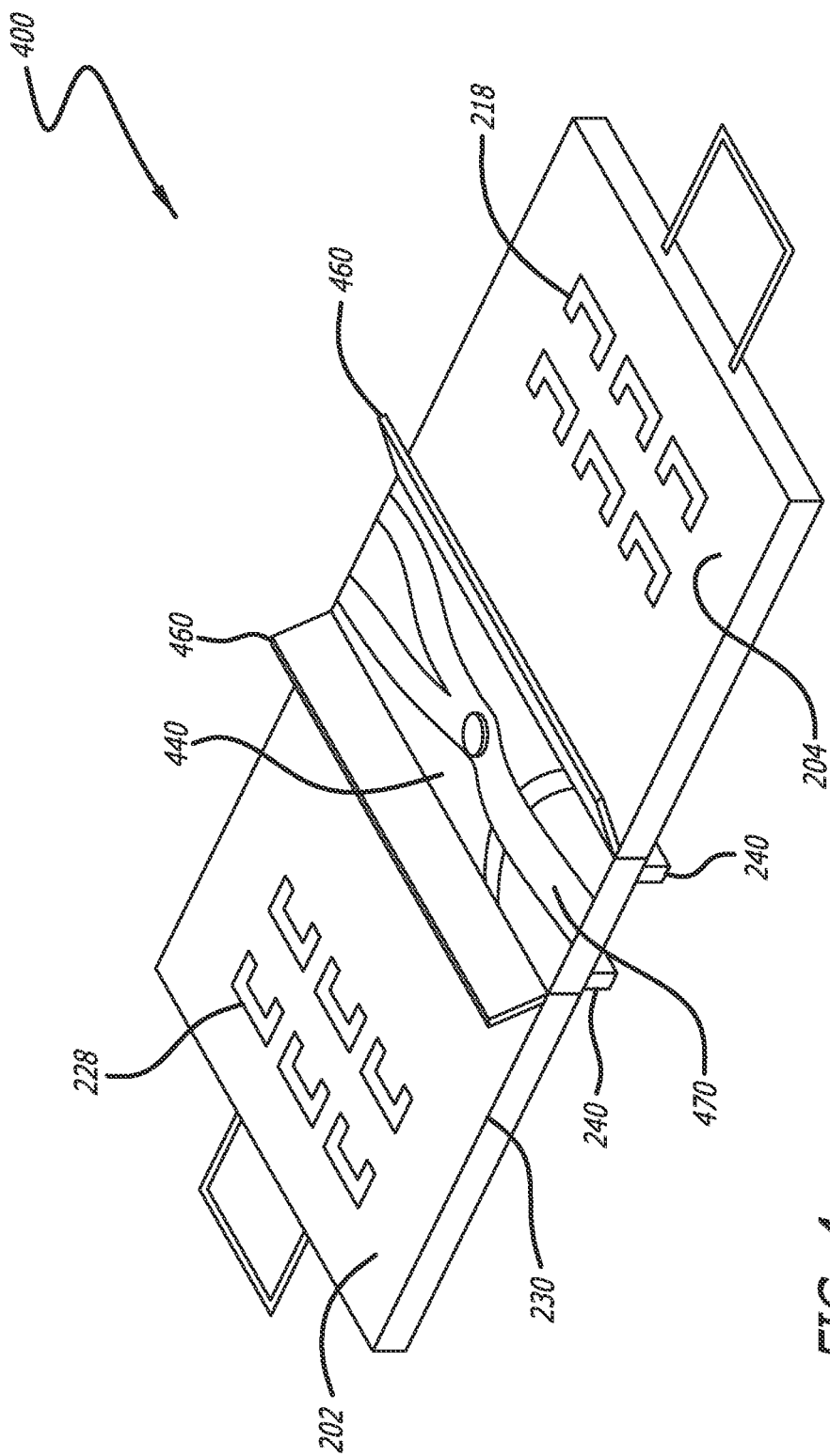
FIG. 4 shows an isometric view of a carrying and storage case for a catheter and pump system according to some embodiments.

FIG. 4 shows an isometric view of the interior of a carrying and storage case 200 for a catheter and pump system, according to some embodiments. As described previously, in some embodiments, case 200 may open along a middle seam 230 that can house accessories or additional catheters and tubing. In this example, case 200 contains clips 218 and 228 on the interior of top and bottom flaps 202 and 204 that can store such additional catheters and tubing. In an embodiment, case 200 can include pockets, for example in place of clips 218 and 228 to store the additional catheters and tubing. In this example, case 200 can comprise a flexible material, such as nylon, so that the two sides of middle seam 230 can meet when case 200 is closed to form a side of case 200. Alternatively, case 200 can comprise an inflexible material, such as leather or plastic.

In an embodiment, the pump system may be stored in the main compartment of case 200, i.e. it may rest on or above central flap 440. Accordingly, as described in the example of FIGS. 2C and 2D above, case 200 can securely fasten the pump system so that it can be transported with minimal concern. In some embodiments, part or all of the interior of case 200 may be padded so as to protect the catheter and pump system from mechanical shocks (see FIG. 2A). For example, central flap 440, top and bottom flaps 202 and 204, and/or middle seam 230 can be padded.

In various embodiments, central flap 440 can include two stiff portions that fold against each other when case 200 is closed, like binding 206 in the example of FIG. 2A above, or a single portion. Specifically, the central flap 440 may include a single flexible, stiff, or semi-stiff portion upon which the catheter and pump system can rest, as shown in this example. For example, the central flap 440 can include a single plastic board or sheet, to provide stiffness, inside a flexible exterior material. In an example, the same flexible exterior material may also comprise the rest of case 200.

In an embodiment, middle seam 230 may be closeable by a zipper, buttons, snaps, hooks, Velcro, and the like. Particularly when closed, case 200 can contain the pump system in a way that conceals the appearance of the pump system and any odors or sounds from the pump system, as well as protecting the pump system from falling or being damaged. In an embodiment, middle seam 230 can even be secured, e.g., by locking with a padlock or a built-in lock.

In addition to the main compartment, case 200 may also contain a number of secondary compartments. For example, case 200 may contain one or more additional compartments to house one or more of the components of the catheter and pump system, such as the canister or pump base, separately from other components. In another example, some components of the system may be housed in pockets, for example a compartment may contain one or more pockets. Alternatively, a pocket may itself be an independent compartment, for example if the pocket includes a cover and/or is closeable, such as using a snap. Case 200 may also contain a compartment to house accessories or additional catheters and tubing. For example, clips 218 and 228 can be located in a secondary compartment. Alternatively, if clips 218 and 228 are located on the interior of top and bottom flaps 202 and 204 as shown, clips 218 and 228 can be separated from the main compartment by a covering sheet. Such a covering sheet may be closeable by a zipper, buttons, snaps, Velcro, etc.

In some embodiments, the case 200 may include supports to stabilize or secure the canister, pump base, and/or any other parts of a catheter and pump system, for example to prevent the canister from falling. For example, guiding strips 460 can support the base of a catheter and pump system resting on central flap 440. Such guiding strips or supports 460 can also provide mechanical support to case 200 as a whole, for example by helping to maintain top and bottom flaps 202 and 204 in upright positions. Likewise, supports 240 can rest case 200 on a floor, the ground, or another surface, and can simultaneously support case 200 as a whole. In an embodiment, supports 240 can include wheels so that case 200 can be rolled along a surface.

In this example, the supports include straps 470, which can be drawn over the base of the catheter and pump system. In some embodiments, straps 470 may configured in a Y-shape and may be flexible, elastic, and/or adjustable, for example they may be loosened or tightened using a clasp and/or buckle. In this example, straps 470 are shaped or contoured to fit the pump base. Straps 470 may include several straps, for example straps 470 can fork around the pump base, as shown, and may include crossing straps in perpendicular directions to further stabilize the base. Alternatively, as seen in FIG. 2D, straps 255-257 may be a set of straps where one or more straps secure the pump base 140 and one or more straps secure the canister 130.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A case and an external catheter system, comprising:
 a pump;
 a canister;
 a catheter tubing;
 an external catheter; and
 a case, comprising:
  a case body including a central flap, a first side hingedly coupled to a first edge of the central flap and a second side hingedly coupled to a second edge of the central flap, the first side releasably secured to the second side along a midline of the central flap;
  a first guiding strip coupled to the first edge and disposed between the central flap and the first side, and a second guiding strip coupled to the second edge and disposed between the central flap and the second side;

at least one strap to secure components of the catheter system to an interior of the case body; and one or more clips affixed to at least one of an interior wall of the first side of the case body or the second side of the case body, wherein the one or more clips are configured to secure one or both of the catheter tubing and the external catheter to the case body.

2. The system according to claim 1, wherein the first side of the case body is releasably secured to the second side of the case body using one of a zipper, Velcro, snap, or button.

3. The system according to claim 1, wherein the at least one strap includes a first strap configured in a Y-shape to secure the pump to the interior of the case body.

4. The system according to claim 3, wherein the first strap is further configured to secure the pump and the canister to the interior of the case body.

5. The system according to claim 4, wherein the first side of the case body or the second side of the case body includes an aperture configured to receive the catheter tubing or an electrical cord.

6. The system according to claim 5, wherein the case body includes dimensions of at least a length of 13 inches, a height of 9.5 inches and a depth of 9.5 inches.

7. The system according to claim 1, wherein the central flap is configured to support one or both of the pump and the canister.

* * * * *